United States Patent [19]
Nylander et al.

[11] Patent Number: 6,066,244
[45] Date of Patent: May 23, 2000

[54] APPARATUS FOR USE IN ELECTRICAL, E.G. ELECTROCHEMICAL, MEASUREMENT PROCEDURES, AND ITS PRODUCTION AND USE, AND COMPOSITE ASSEMBLIES INCORPORATING THE APPARATUS

[75] Inventors: Claes Ivan Nylander, Bedfordshire; Brian Jeffrey Birch, Northants; Clive Edward Marshman; Peter Richard Stephenson, both of Bedfordshire, all of United Kingdom

[73] Assignee: Unilever Patent Holdings B.V., Netherlands

[21] Appl. No.: 07/842,329

[22] Filed: Feb. 28, 1992

Related U.S. Application Data

[62] Continuation-in-part of application No. 07/530,436, Jun. 1, 1990, abandoned, which is a continuation of application No. 06/887,038, filed as application No. PCT/GB85/00494, Oct. 31, 1985, abandoned.

[30] Foreign Application Priority Data

| Oct. 31, 1984 | [GB] | United Kingdom | 8427559 |
| Oct. 15, 1985 | [GB] | United Kingdom | 8525236 |
| Oct. 31, 1985 | [WO] | WIPO | PCT/GB85/00494 |

[51] Int. Cl.$^7$ .......................... G01N 27/30; G01N 27/333
[52] U.S. Cl. ........................... 204/435; 204/416; 204/418; 204/419
[58] Field of Search ................... 204/418, 416, 204/419, 435

[56] References Cited

U.S. PATENT DOCUMENTS

| 3,649,506 | 3/1972 | Petersen et al. | 204/435 |
| 3,662,745 | 5/1972 | Cosentino | 204/435 |
| 3,676,319 | 7/1972 | Kirsten | 204/435 |
| 3,723,589 | 3/1973 | Kennedy | 204/435 |
| 3,856,649 | 12/1974 | Genshaw et al. | 204/435 |
| 4,020,830 | 5/1977 | Johnson et al. | 204/418 |
| 4,133,732 | 1/1979 | Boeke | 204/435 |
| 4,133,735 | 1/1979 | Atromowitz et al. | 204/433 |
| 4,214,968 | 7/1980 | Battaglia et al. | 204/418 |
| 4,280,889 | 7/1981 | Szonntagh | 204/420 |
| 4,450,842 | 5/1984 | Zick et al. | 204/435 |

FOREIGN PATENT DOCUMENTS

| 0024191 | 2/1981 | European Pat. Off. . |
| 0024192 | 2/1981 | European Pat. Off. . |
| 0030503 | 6/1981 | European Pat. Off. . |
| 0125560 | 11/1984 | European Pat. Off. . |
| 2021772A | 12/1979 | United Kingdom . |

OTHER PUBLICATIONS

Fjeldly et al, "Solid–State Ion–Sensitive Electrodes with Integrated Electronics", *J. of Electrochemical Soc.*, vol. 126, No. 5, May 1979, pp. 793–795.

*Primary Examiner*—T. Tung
*Attorney, Agent, or Firm*—Cushman Darby & Cushman Intellectual Property Group of Pillsbury Madision & Sutro, LLP

[57] ABSTRACT

A composite electrode, comprising:

a solid non-metallic substrate, (such as ceramic, glass, or epoxy resin,)

and, bonded directly or indirectly to said substrate, a non-conducting matrix, incorporating particles which are accessible to the electrode surface and contain an insoluble metal salt (e.g. halide) in direct electrical contact with the metal corresponding to said salt, said metal being present either (i) in the form of metallic particles incorporated in a non-conducting matrix zone disposed so that said metal salt-containing particles are located between said metallic particles and said electrode surface, and/or (ii) a solid metallic surface in the form of an intermediate layer between said matrix and said substrate.

13 Claims, 4 Drawing Sheets

APPARATUS FOR USE IN ELECTRICAL, E.G. ELECTROCHEMICAL, MEASUREMENT PROCEDURES, AND ITS PRODUCTION AND USE, AND COMPOSITE ASSEMBLIES INCORPORATING THE APPARATUS

This invention relates to apparatus suitable for use in electrical, e.g. electrochemical, measurement procedures, and to its production and use. This is a Continuation-in-Part of U.S. patent application Ser. No. 07/530,436 filed Jun. 1, 1990, now abandoned, which was a continuation of U.S. patent application Ser. No. 06/887,038, filed Jun. 24, 1986, now abandoned, which was a 371 filing of PCT/GB85/00494, filed Oct. 31, 1985.

It is known for various electrical (especially electrochemical) measurement purposes to make and use ionophore-sensitised polyvinylchloride (pvc) membranes. Known ion-selective polyvinylchloride membrane electrodes include for example constructions in which an electrode is separated from an ionophore-loaded polymer by an intermediate inner electrolyte. One such known pvc-containing ionselective electrode system comprises a solid hollow tube containing an aqueous electrolyte solution. The end of the tube is closed by an ion-selective pvc membrane secured by a screw-down compression fitting. The inner electrolyte normally contains chloride together with (if different) a salt of an ion to which the electrode system has been made sensitive by the use of a membrane of appropriate selectivity, and the inner electrolyte has immersed in it a silver/silver chloride electrode. The silver is provided with a connection to an external circuit, usually an electrometer amplifier of high impedance, connected via a length of screened flexible cord. Normally, such an electrode is in use immersed in a (e.g. dilute) aqueous solution relevant to the measurement purpose, as part of a cell of which the other side is completed by a standard-potential reference electrode, e.g. one comprising silver/silver chloride in high concentration KCl solution, e.g. 3M KCl. The pvc of the membrane normally contains plasticiser and ionophore to enable the electrode system to be sensitive to a particular component of the analyte liquid. Also known is the use of coated-wire electrodes based on ionophore-loaded polyvinylchloride coatings over conductive metal wire or graphite rod. We consider that for several purposes these coated-wire arrangements are rather unstable, e.g. in several examples their lifetime is limited by failure of the polymer layers to retain their adhesion to the solid conductor, and they are sometimes awkward to make. The electrode systems containing inner electrolyte are rather complex in construction. These systems can also often be insufficiently robust.

Prior art in relation to the preparation of electrode materials also includes for example GB 2 021 772 (preparation and heat-treatment of mixtures of silver and silver particles in porous epoxy applied to metal substrate) and GB 1 586 691 (potted assemblies of integrated circuits and button electrodes made by loosely sintering powered glass and silver compounds, and backing the sinter with a peurable polymer compound), as well as the application of electroactive particles in matrices of polymer directly to metal electrodes, or as outer membranes in electrodes which comprise inner electrolyte.

One of the aims of this invention is to produce electrodes of robust construction without inner electrolyte, and to achieve mechanical stability, freedom from liability to develop air bubbles (in an inner electrolyte liquid) and freedom from concentration changes over time.

According to the present invention we provide a composite electrode, comprising;
 a solid non-metallic substrate, (such as ceramic, glass or plastics material, e.g., epoxy resin)
 and bonded directly or indirectly to said substrate,
 a non-conducting matrix, incorporating particles which are accessible to the electrode surface and contain an insoluble metal salt (e.g. halide) in direct electrical contact with the metal corresponding to said salt, said metal being present either (i) in the form of metallic particles incorporated in a non-conducting matrix zone disposed so that said metal salt-containing particles are located between said metallic particles and said electrode surface, and/or (ii) a solid metallic surface in the form of an intermediate layer between said matrix and said substrate.

We find that electrodes of this form offer robustness, versatility of application and convenience in use. A number of embodiments are described below. In many of them, the electrode has an electroactive membrane which overlies said matrix incorporating said metal halide-containing particles. In the description given below, references to ionophores mean materials such as ion carriers which are capable of conferring electrochemical selectivity on such electroactive membranes, without regard to other particular physicochemical properties of such ionophores, e.g. their electrical charge or neutrality.

In certain examples, the metal halide-containing particles present are metallic particles derived from a layer of non-conducting matrix incorporating metallic particles, the surface of which layer has been treated to convert metal to metal halide, e.g. produced by anodic electrolysis of the metal.

In several useful forms of the electrodes, the particle-containing matrix has been formed by printing a layer of corresponding material in flowable form on to the solid substrate, and hardening of layer or allowing it to harden.

Suitable substrates comprise for example epoxy, polyvinylchloride, or alumina or other ceramic material.

It is especially useful to place a hermetic sealing layer over all conductive or electroactive parts of the electrode other than the sensitive surface intended to contact electrolyte.

Also provided by the invention is an assembly comprising a composite electrode as described herein, wherein the metallic part of the composite electrode is functionally connected to a hermetically sealed (packaged) integrated semiconductor signal processor or impedance converter circuit mounted on said solid non-metallic substrate.

For example, there can be present an alumina or other ceramic substrate, or a pvc or other polymer substrate, on which there is mounted a hermetically encapsulated integrated circuit, with its connexions electrically bonded to the conductor(s) forming electrode(s) on the substrate, the structure being further encapsulated with a hermetic sealing material applied by spraying, dip-coating, moulding or otherwise in manner known per se, the sealing material being for example epoxy material or pvc or other polymer, to form an integral sealed assembly having a functionally exposed electrode or electrode area or areas not covered by the final encapsulation treatment.

Also provided by the invention is a process for providing these composite electrodes, which comprises (i) applying to a solid non-conducting substrate surface a flowable layer of a matrix material comprising particles that contain an insoluble metal and/or metal salt (e.g. halide), (ii) allowing the layer to harden and bond to the substrate surface, and (iii)

(where the particles contained metal but did not already contain insoluble metal salt) forming insoluble metal salt corresponding to the metal of the particles either by treatment of the surface of said particle-containing matrix layer to form superficial insoluble metal salt thereon.

Further details and embodiments of the invention are given hereinbelow.

In the performance of the present invention, the non-conducting matrix can be a body of polymer such as polyvinyl chloride, which incorporates conductive particles. The conductive particles are such as to allow the provision of a conductive connection from the particle-containing composite to an external electrical circuit. In an example to be described below, the conductive particles provide the composite electrode with a conductivity corresponding to resistivity of a few milliohm-cm. This value is by no means critical: resistivities several orders of magnitude higher can be used, but the resistance of the electrode material should generally be small in comparison with that of the external circuit (often many megohms).

Besides polyvinylchloride, other useful nonconducting solid matrices are for example polyurethane, polystyrene, polyvinylacetate, e.g. mixtures of pvc and polyvinylacetate, as well as inorganic matrices e.g. such as glass. In what follows, mention of polyvinylchloride (pvc) implies also the possible use of any such substitute matrix material. In the structures provided by the invention, the conductive particles can be for example graphite, silver, platinum, palladium-silver, tin-palladium-silver, gold, or copper. If desired, the matrix in which the particles are incorporated can be an organic matrix derived by solidification from the paint vehicle used as the base of conductive paints known and available for use in thick-film microcircuit manufacture, e.g. for the purpose of painting or screen-printing conductive tracks on flat insulating substrates such as ceramic substrates. Suitable particle sizes for the conductive particulates are for example those in the range from (of the order of) 20 to (of the order of) 200 microns. Suitable levels of incorporation of the particles into the composite can include for example those of the order of 10%–80%, e.g. 50%, by volume (based on the volume of the composition), or, dependent on the nature of the particles, whatever level is needed to reach a desired degree of electrical conductivity. One example of a electrode structure comprising silver-pvc has 3:1 silver particles: pvc particles by weight, with 50 micron (maximum particle size) silver particles.

Thus, one form of the composite electrode comprises a conductor and a non-conductive membrane matrix material, (e.g. glass or organic polymer), in direct contact with the conductor, wherein the conductor comprises a matrix incorporating conductive particles (containing metal salt, e.g. silver chloride or silver/silver chloride particles), and the overlying organic membrane material, if present, comprises a sensitising component such as an ionophore, for sensitising the electrode to a particular analyte to be investigated, and the organic membrane material is securely bonded to the matrix of the conductive composite. For example, the membrane material and the matrix can, conveniently, both be of a similar polymer and can be fused or bonded together in any convenient manner. The conductor can be for example in the form of a conductive metal track or film fixed to a plastics or ceramic substrate.

In these arrangements, usually the intermediate metal layer is smaller in area than the substrate and the matrix, and there is direct bonding between the substrate and the matrix, as well as between the matrix and the metal.

This structure is particularly robust and for example can give longer life in use than a comparable (e.g.coated-wire) electrode.

It is particularly useful and within the scope of the invention to provide electrode structures comprising a composite layered structure of pvc comprising a layer or zone of pvc incorporating conductive particles, as mentioned above, and a layer or zone of pvc incorporating an ionophore, to form a membrane that in use separates the conductive pvc composition from an external liquid of which an electrochemical characteristic is to be measured or tested. Preferably the same polymer is used as basis for the particle-loaded layer as for the ionophore-loaded layer. This has been found to facilitate fusion and high bond strength between the layers. We find that such arrangements are highly useful in that amongst other things they combine freedom from inner electrolyte and from liquid junctions, with good and robust stability.

For the purposes of these composite layered structures it is preferred (for the pvc of the zone that incorporates the conductive particles) to use pvc incorporating either no plasticiser or only very small quantities of plasticiser, (described herein as "pure" pvc). (Preferably, of the order of 10% by weight of plasticiser or less can be present in this zone. Preferably there is less, e.g. <5%, e.g. <1%).

In the case of the membrane material, examples of suitable contents for the ionophore or other sensitising component are for example within the range 5–10% by weight of the whole membrane composition. The ionophore-containing zone can be for example 0.1–1 mm thick. The pvc of the zone that incorporates the ionophore or other sensitising component should usually incorporate conventional relatively large amounts of plasticiser, as used in previous ionophore-pvc membranes, e.g. the ionophore-containing layer can for example be composed largely of a pvc:plasticiser composition in proportions for example in the range 1:1 to 1:2 by weight. Examples of plasticisers useful in connexion with ion-selective polymer membranes, especially pvc membranes, include dioctyl phenyl phosphonate, diethyl adipate, dioctyl sebacate, trioctyl phosphate, and o-nitrophenyl phenyl ether. Examples of useful ionophores include calcium diisooctyl phenyl phosphate (for calcium-sensitive electrodes) valinomycin (for potassium-sensitive electrodes), tridodecylamine (for hydrogen-ion-sensitive electrodes), particles of silver chloride, bromide, or iodide (for corresponding halide-sensitive electrodes), particles of silver sulphide (for sulphide-sensitive electrodes), mixtures of particles of silver and copper sulphides (for electrodes sensitive to copper as well as to sulphide), and more generally a finely divided particulate form of any of the materials previously used in crystalline form for making single-crystal electrodes, can be incorporated into the polymer or other non-conducting matrix of the electrode membrane, in sufficient amount to put the particles in electrically effective contact to enable the electrode to respond to the presence of the corresponding constituent of the surrounding solution to be tested or measured.

Particularly useful examples of the electrodes comprise a metallic conductor in contact with an insoluble salt of a metal comprised in the conductor: e.g. silver and silver halide. It is for example particularly useful, in cases where the specific electrode material is based on inorganic ion-sensitive materials, to provide an electrode structure with one or a plurality of junctions between pairs of active materials, each pair having an anionic or cationic component in common, and the material in contact with the analyte solution having a common component with the analyte. For example, silver and silver halide have a common cationic component, (i.e. silver, notwithstanding that the silver of the metallic conductor is substantially not in the cationic form), and a suitable combination of materials for a fluoride-sensitive electrode is for example a multilayered, e.g. 4-layered, (e.g. laminate) construction, each layer comprising particles of the following materials in a (e.g. pvc) matrix: silver, silver chloride, silver flurode, lanthanum fluoride.

To manufacture these structures it can be convenient and is within the scope of the invention to build up successive layers of matrix such as polyvinylchloride, loaded with various additives, e.g. as follows. If desired, there can be provided a zone of pure (i.e. tolerably plasticiser-free) pvc. Either as an overlying layer, or as a substrate in itself, there can be provided a zone of silver-particle-loaded (pure) pvc. This zone can be treated to give it a content of silver chloride accessible at its surface and in conductive contact with the useful conductive structure (e.g. as described in the Examples below). After treatment to provide silver chloride, a further zone (layer) of plasticised pvc loaded with inonphore or other sensitising component can be provided, to act as an electroactive membrane. The successive zones can be deposited either by solidification of applied (thin) layers of molten (thermoplastic) pvc with suitable additives, or by evaporation of solvent from suitably-loaded pvc solutions in a compatible solvent such as tetrahydrofuran, which can be applied by any suitable technique chosen from among those known per se, such as dip-coating, printing, etc.

It is within the scope of the invention to apply the electroactive membranes in any suitable way, not only by forming a membrane which has an ionophore content but also by forming a membrane without such content and then contacting the membrane so formed with an ionophore to allow the latter to activate the membrane, (e.g. as described by E. Fogt and P.Cahalan in Anal. Chem. (1985) 57, pp 1155–1157, and in U.S. Pat. No. 4,486,290).

In order to confer structural strength on the composite there can be a substantial core, e.g. a rod or tube or a flat substrate, of pvc or other (e.g. polymer) matrix material, e.g. pvc of normal commercial grade, which can incorporate substantial quantities of plasticiser, which has successive and preferably thin layers built up on it as follows:- (a) (optionally) pure pvc if desired, (b) silver-particle-loaded pure pvc, and (c) ionophore-loaded or otherwise sensitised plasticised pvc. The layers can in certain useful examples be of the order of 0.1–1 mm thick in each case.

In one highly important configuration, for example, a planar substrate of material to which the pvc layers can be bonded or fused can have successive analogous flat layers built upon it, the successive layers for example comprising compositions as described above and forming an integral fused or bonded structure.

It is understood that when a chloriding process is required, the chloriding can be applied to silver as used in embodiments of this invention, by any method known per se, e.g. electrolysis with the electrode placed as anode in an electrolytic HCl bath, or other known way. Alternatively the chloride may be applied as a layer of matrix incorporating silver chloride particles.

The use of pure (plasticiser-free) pvc or other non-conductive (e.g. polymer) matrix as an encapsulation material and/or structural support material for an electrode structure incorporating an ionophore-loaded or otherwise ion-selectively sensitised membrane fused or bonded to the substrate is believed to be an independently novel and advantageous feature of the invention in itself and in combination with any of the features described elsewhere in this specification.

The manufacture of structures according to embodiments of this invention can be carried out by using a solvent-welding or solvent-casting technique, or other technique e.g. a thermal technique to insure that the layers involved in the composites are in intimate contact and preferably become or are formed into an integral, one-piece fused or bonded construction. Fusion or annealing processes are for example particularly suitable for vitreous or ceramic constructions, e.g. a glassy matrix containing ion-selective inclusions such as particles can be fused on to a glassy or ceramic substrate, e.g. containing conductive inclusions such as conductive particles.

The nature and variety of ion-selective membranes, known per se, which can be fabricated to form parts of composite structures that constitute embodiments of the present invention, is very wide, and depends on the particular end-use to which the electrode is to be put. Specifically incorporated by reference herein are all the detailed membrane electrode compositions described (in connexion with conventional wire cores) by G J Moody and J D R Thomas in "Poly(Vinyl Chloride) Matrix Membrane Ion-Selective Electrodes", ch.4 of "Ion Selective Electrodes in Analytical Chemistry", ed. H Freiser, Plenum Press 1980, and in U Fiedler and J Ruzicka, Anal. Chim. Acta, 67, 179 (1973).

Further details of membrane fabrication, also incorporated herein by reference, are given by H Tamura et al; Anal. Chem. (1982), 54, pp1224–1227, and by D. Ammann et al., in "Ion Selective Electrode Reviews", 5 (1), 1983, pp 3 et seq.

According to another aspect of this invention, an electrode structure based on a non-conducting matrix also comprises a hermetically sealed signal processor circuit functionally connected to the (one or plurality of) electrodes of the electrode structure, said hermetically sealed signal processor circuit comprising a hermetically sealed (packaged) integrated circuit together with ancillary conductive connections and possibly further components mounted together on the non-conducting matrix and provided with overall hermetic sealing.

The electrode or electrodes can in themselves for example (but without limitation) take any of the forms described above in this specification or in the succeeding description and Examples.

The hermetically sealed package including the electronic circuit can be used directly as the non-conducting substrate mentioned earlier or the package can be mounted onto the substrate used for the electrode.

By using these forms of construction, composite devices for electrochemical measurements can easily be made for example by printing conductors (e.g. using conductive particles in an organic matrix vehicle) on to an alumina or other ceramic substrate, or on to a pvc or other polymer substrate, mounting a hermetically encapsulated integrated circuit on the substrate and electrically bonding its connexions to the conductors, forming the electrode(s) on the substrate, and further encapsulating the substrate by spraying, dip-coating, moulding or otherwise applying in manner known per se a hermetic sealing and insulating encapsulant such as epoxy material or pvc or other polymer, to form an integral sealed assembly having a functionally exposed electrode or electrode area or areas not covered by the final insulating encapsulation treatment.

There are a number of different standard packages for integrated circuits. Examples of such packages which are particularly useful for this purpose are DIL (dual-in-line), SO (small outline) and LCC (leadless chip carrier).

Many integrated circuits are commercially available in DIL and SO packages. The use of these in the present invention is therefore an easy and inexpensive option. The advantage with LCC is that non-standard circuits are easily mounted into these.

It is also possible to mount an integrated circuit directly onto the substrate but this is not very practical. The reason is that this puts very severe restrictions on the insulation of the assembly. Moreover, the extreme delicacy of the very thin bonding wires (typically 25 $\mu$m) which are used for this purpose makes it difficult to encapsulate the assembly properly without damaging these wires.

By using pre-packed electronic circuits the assembly becomes mechanically robust and can therefore be encapsulated by a variety of means.

Preferably the outer material of the electrode or electrode area(s) (e.g. polymer membrane) is chosen for bonding compatibility with the hermetic sealant applied to the remaining parts of the assembly so that no ingress of water or corrosive contaminants such as ions in solution can occur to degrade the electrical connections within.

The details of the circuitry forming part of these composite assemblies are in themselves of known kind and form per se no part of this invention: but by way of illustration it can be pointed out that standard semiconductor devices or integrated circuits, e.g. operational amplifier integrated circuits, especially those with f.e.t. inputs, or simply single encapsulated f.e.t.'s, are very suitable for inclusion in the hybrid electrode assemblies described herein.

Examples of embodiments of the invention and their manufacture and use are illustrated in greater detail by the following description and accompanying drawings.

BRIEF DESCRIPTION OF THE DRAWINGS

FIGS. 7A1 and 7A2 show in diagrammatic form arrangements used to fabricate electrodes according to the invention.

EXAMPLE 1

A chloride-sensitive electrode can be made and used as follows. A rod of pvc of ordinary commercially available grade is dipped and stirred a few minutes in tetrahydrofuran (THF) to round its sharp edges and leave a partly dissolved surface layer to fuse with the additional material to be applied. The rod so treated is then dipped in a solution of pvc and trioctyl phosphate plasticiser containing suspended powdered silver, in THF (proportions 0.05 g pvc, 0.01 g plasticiser, and 0.3 g silver per ml mixture), and air-dried at about 50° C. for about 30 minutes to evaporate the solvent.

The composite electrode so made is given an ohmic contact at one end and chlorided by anodization, for example in 0.1M HCl solution opposite a platinum cathode at a current density of about 300 microamps per $cm^2$ of silver composite electrode surface for about half an hour. The anodized electrode, now with a surface content of silver chloride, is rinsed and stored in purified (deionised) water preferably at least 24 hours before use. The electrode can be used in a similar manner as a conventional silver/silver chloride electrode.

EXAMPLE 2

A calcium-selective planar electrode structure can be made and used as follows, and is illustrated in diagrammatic plan and section in FIGS. 1 and 2.

A laminar plastics substrate 1 in the form of for example a 5 mm×30 mm strip, 0.5 mm thick, of mixed polyvinylchloride/polyvinylacetate with filler, and a relatively low content of plasticiser, has its surface partly masked off by a solvent-resisting mask to leave an area to which an conductive strip 2 is applied as follows. The area to be treated is wetted with THF, and a silver-powder-containing pvc-plasticiser-solvent mixture as in Example 1 is applied in an amount sufficient to give 0.1–0.2 mm thickness in the conductive strip 2 after air-drying as in Example 1. The masking is removed before the air-drying, and the dry product is anodized and stored as described in Example 1. After storage for 24 hours the composite is air-dried again, slightly wetted with THF, and an ion-selective pvc membrane 3 is applied by dipping one end of the composite into a mixture of the following components dissolved or dispersed in THF: 0.03 g/ml pvc, 0.06 g/ml dioctyl phenylphosphonate plasticiser, and 0.0067 g/ml di-(4(1,1,3,3,-tetramethylbutyl) phenyl) ionophore. After one dip in this mixture the composite is air-dried for about an hour to remove the solvent and form the membrane 3. The electrode is then masked off at each end and dipped to form a further coating 4 of slightly plasticised pvc about the middle of the strip. The coating 4 partly overlaps the membrane 3 previously formed and leaves a bare extremity of the strip at the other end, and is formed by dipping or otherwise contacting the desired part of the strip in a solution of 0.1 g/ml pvc and 0.01 g/ml trioctylphosphate in THF, followed by air-drying about 2 hours at about 30° C. Coating 4 is an effective insulator and overlaps membrane 3 by about 5 mm. An ohmic contact 5 is formed at the bare extremity of conductive strip 2 by any convenient method; the contact can be retained by a clip or by using silver-epoxy glue or by low-temperature soldering.

The resulting electrode is useful as a robust calcium-sensitive electrode.

EXAMPLE 3

In a particularly preferred embodiment, potassium-selective electrodes can be reproducibly produced in large numbers by the following method. Cut out 20 cm×20 cm sheets from a 1.5 mm thick sheet of PVC (e.g. Davcron, ICI) and screen-print thereon 1.5 mm wide and 13 $\mu$m thick parallel tracks, 5 mm apart, of silver particle loaded polymer paste (e.g. P230, Johnson Matthey) through a suitable silk-screen. Cure the printed paste in an oven at 50° C. for 12 hours. Divide the sheets into four parts, 20 cm×5 cm, by cutting them across the printed tracks. Chloridise the surface of the tracks by immersing the sheets in a water solution of 3% hydrogen peroxide and 0.1 molar hydrochloric acid so that about 2 cm of each track is kept above the solution. After 5 minutes a suitable amount of silver chloride will have formed on the surface of the immersed part of the tracks. Remove the sheets from the solution and rinse well in distilled water. Leave the electrodes to dry for at least one hour in a dry and clean atmosphere.

If the electrodes are to be stored before the chloridising treatment described above they should be kept in a dry atmosphere free from hydrogen sulphide to prevent uncontrolled formation of silver sulphide on the surface. This atmosphere can be obtained in a closed cabinet containing silica gel and sodium hydroxide pellets.

Cast ion selective membranes onto the chloridised part of the electrodes by immersing the sheets in the same manner as above in a solution of 28 mg/ml PVC and 55 mg/ml dioctyl phthalate and 0.8 mg/ml valinomycin in tetrahydrofuran. The sheets should be immersed in this solution for only a few seconds and slowly withdrawn from the solution. Leave the sheets to dry for about 5 minutes and repeat this procedure ten times. Thereafter, store the sheets in a dry atmosphere at 25° C. for one hour to allow the solvent to evaporate.

Cut the sheets between the tracks to produce individual devices of dimensions 50 mm×5 mm. An electric lead can be connected to the uncoated end of each electrode by means of, for example, a suitable silver loaded epoxy resin, and the uncoated end and the lead can be encapsulated by any suitable means.

The resulting electrodes can be used in the same way as conventional ion selective electrodes for the analysis of potassium ions in aqueous solutions.

The electrode fabrication methods employed in the preceding description and examples can also be applied to the construction of further embodiments within the scope of the invention, as illustrated by the accompanying schematic sectional drawings, FIGS. 3, 4, 5, 6 and 6A, in which like reference numerals denote like parts.

Each of FIGS. 3–6 and 6A shows in schematic section an assembly 101 incorporating both an electrode 102 and a hermetically sealed operational amplifier integrated circuit 103 connected as a signal processor so that it can give an output (usually amplified and at relatively low-impedance) corresponding to the signal potential developed by the electrode in use. Any desired number of wire connections 104 or other means of connections are provided at one end of each assembly, to provide for signal takeoff, power supply and any other function corresponding to the nature of the particular circuitry, which in itself forms no part of the invention.

Each assembly (other than FIGS. 6 and 6A) is based on a laminar polymer sheet, (here pvc,) which serves as a substrate 105.

Conductive tracks 106 are bonded to the substrate 105 by screen-printing a conductive-particle-pvc mixture, and drying/hardening the result, and a hermetic sealing 107 ion-selective membrane coating 108 is applied in the case of each assembly, all by the techniques already described herein.

Figure 3:
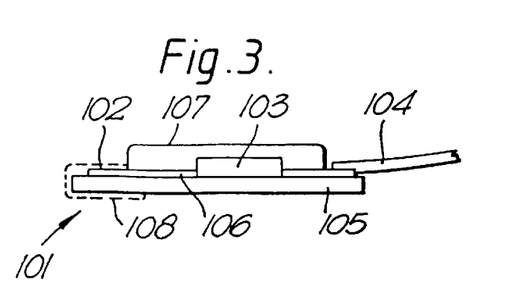
FIGS. 3–6 and 6A are schematic sections of an assembly incorporating an electrode according to the invention.

In the device of FIG. 3, the electrode 102 is formed by a part of the conductive track 106 and the overlying membrane layer 108 which is applied over an end part of the substrate 105 and conductive area not covered by hermetic sealing 107.

Figure 4:
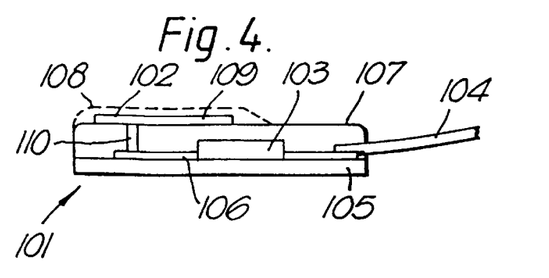

In the device of FIG. 4, the hermetic sealing layer 107 covers the whole of substrate 105 and the components mounted on it. A further conductive layer 109 is applied by similar screen-printing technique as before to part of the upper surface of sealing layer 107, and is conductively connected to track 102 by a previously-bored hole 110 filled with a matrix loaded with conductive particles, e.g. by a similar composition as is used to make the conductive layers. Membrane layer 108 is then applied to conductive track 109.

Figure 5:
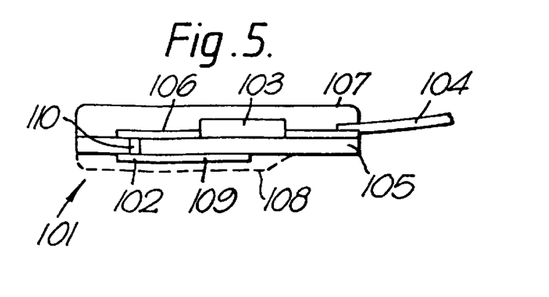

The device of FIG. 5 is similar to that of FIG. 4 except that the extra layer 109, and conductor-filled boring 110 are applied to substrate 105 instead of sealant layer 107, and membrane layer 108 is formed in an appropriate position to result in an electrode mounted on the opposite side of substrate 105 to the side on which the other components are mounted.

In a useful variant of the device of FIG. 5, conductive tracks 106 and 109 are joined by their extension up to and around the edge of substrate 105 instead of the connection shown as in FIG. 5, and the sealant layer 107 extends to cover the area in which they so join.

Figure 6:
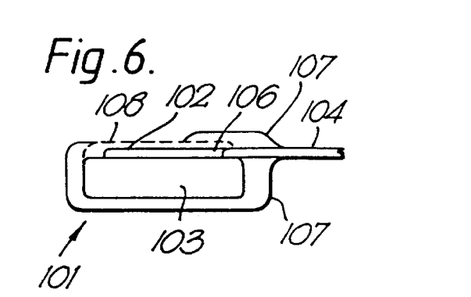
Figure 6A:
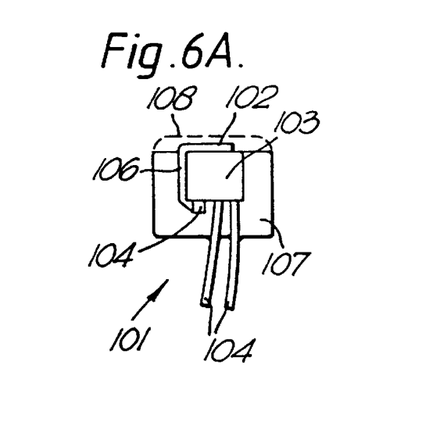

In the devices of FIGS. 6 and 6A, which represent a convenient simplification of the construction used in the devices of FIGS. 3–5, the packaging 103 (e.g. epoxy packaging) of a hermetically sealed operational amplifier integrated circuit or other appropriate semiconductor circuit or device itself forms the substrate on which a membrane electrode structure is fabricated. A conductive track 106 is bonded to the surface of the packaging 103 in contact with a suitable one of the connexion wires 104, and at least an electrode portion 102 of track 106 is overlain by a suitable membrane coating 108. If desired, a further overall hermetic sealing 107 can be applied, leaving a suitable number of electrical connexions and active electrode areas clear to function. The order in which the hermetic packaging 107 and the membrane material 108 are applied is not critical so long as an effective seal is obtained. For the device of FIG. 6A, it may be most practical to apply membrane 108 last. For these embodiments in particular it is recommended to use (in the case of an epoxy packaging 103) a silver-particle-loaded conductive paint of a kind conventional in itself, if convenient such a paint based on epoxy material, and pvc is suitable for application as the base component of a membrane material on top of such a conductive-layer.

Devices similar to those of FIGS. 3–5 can be made on the basis of siliceous or ceramic substrates and glass membranes, among other materials.

The examples of devices described and illustrated are robust selectively ion-sensitive electrodes with good resistance to degradation by the permeation of sample liquids and components thereof, and are accessible to a flexible and convenient manufacturing process allowing the production of electrode systems with a variety of specificities.

It will be understood that many modifications and variations are applicable to the devices described herein. For example, a plural number of conductive electrodes can be applied to a planar substrate as in Example 3, and by suitable masking or other method of restricting the area of application of layers, membrane layers can be applied to each conductive electrode, with the different membrane layers being either similar or different in composition, to give multiple specificity in a single electrode assembly. The upper edge of a planar electrode or assembly of electrodes can carry a plurality of ohmic contact locations, at least one for each electrode, and can be connected to an external circuit in any desired manner, e.g. by a snap-fitting connector or plug-and-socket edge connector.

It is also within the scope of this invention, to use electrode systems as described herein, which have been modified to form a layer of enzyme or other protein in contact with the polymer membrane layers or other non-conductive matrix membrane layers, especially the pvc layers, to modify the action of the membrane and the electrode in an analogous manner to the modification of previous pvc membrane electrodes described by Ismail et al., in Analyst, 109, (1984), pp 1205–1208.

Further details of the methods used to fabricate particular examples of electrodes as described herein, and details of tests carried out on electrodes so fabricated, are shown in accompanying schematic drawings 7A–7E.

Figure 7A:
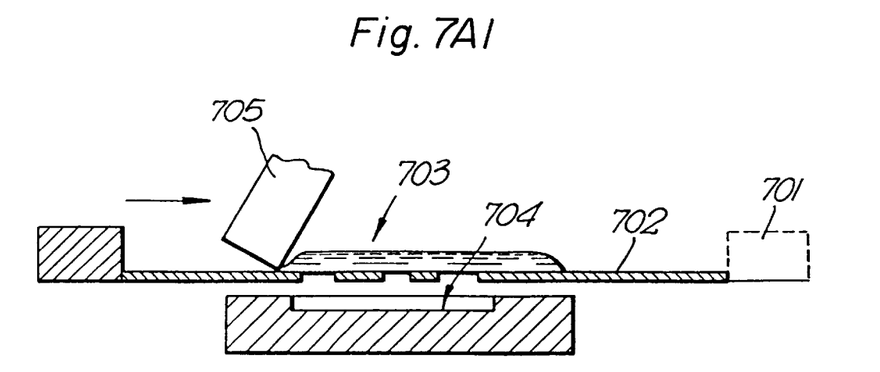
Figure 7A:
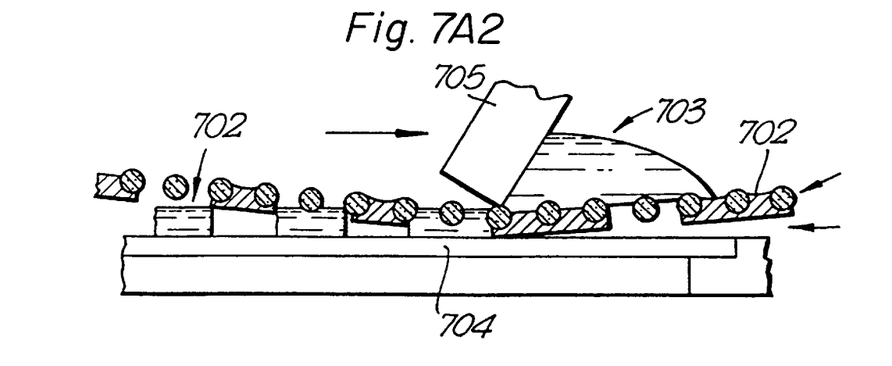

FIGS. 7A1 and 7A2 show in diagrammatic form the arrangements used to screen-print the conductive flowable "inks" comprising silver particles and hardenable polymer base (e.g. as commercially obtainable for the purpose of manufacturing hybrid electronic circuitry) on to substrates as discussed herein. In FIGS. 7A1 and 7A2, a screen-printing frame 701 supports a gauze and mask 702 and is coated with ink 703 which is applied to the substrate 704 at the open areas of mask 702 by the action of a squeezee 705.

Figure 7B:
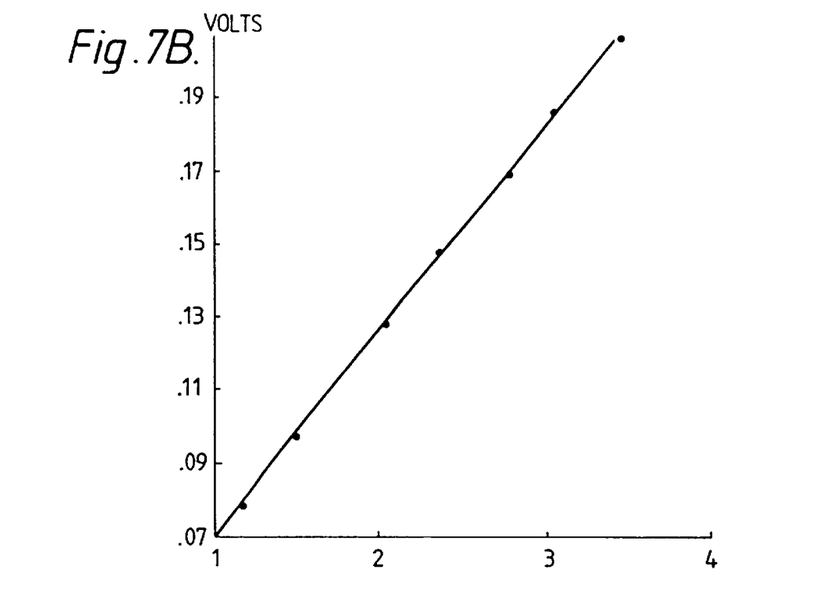
FIGS. 7B–E are graphs illustrating test results obtained using the electrodes of the invention.

FIG. 7B shows the chloride sensitivity (millivolts versus p[Cl⁻] i.e. negative log activity) of a screen-printed silver electrode made in this way and anodised in 0.1M HCl with a Pt wire cathode for 300–1200 seconds at 0.85 mA/cm².

Figure 7C:
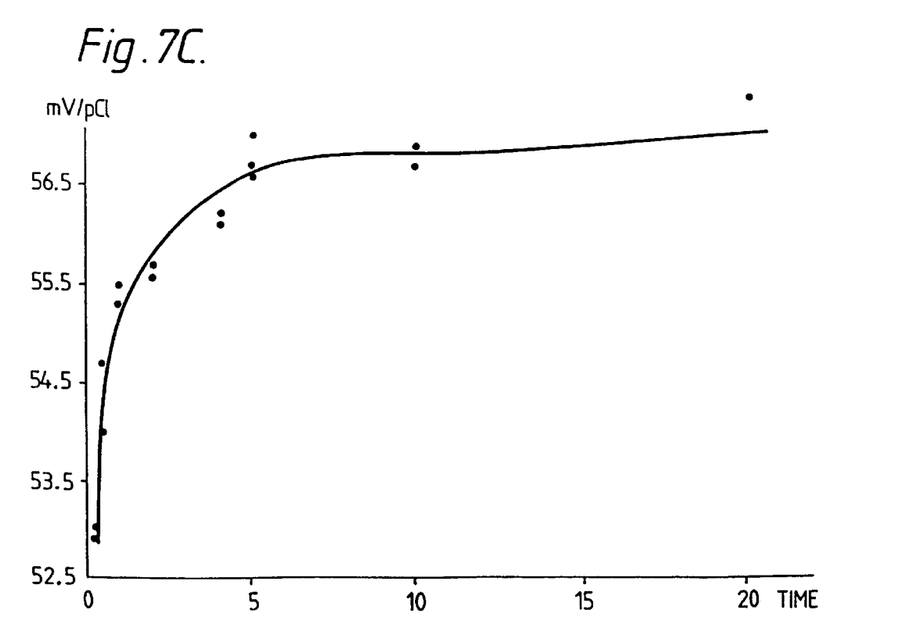

FIG. 7C plots the slopes of graphs like FIG. 7B for a range of anodisation times (minutes).

Figure 7D:
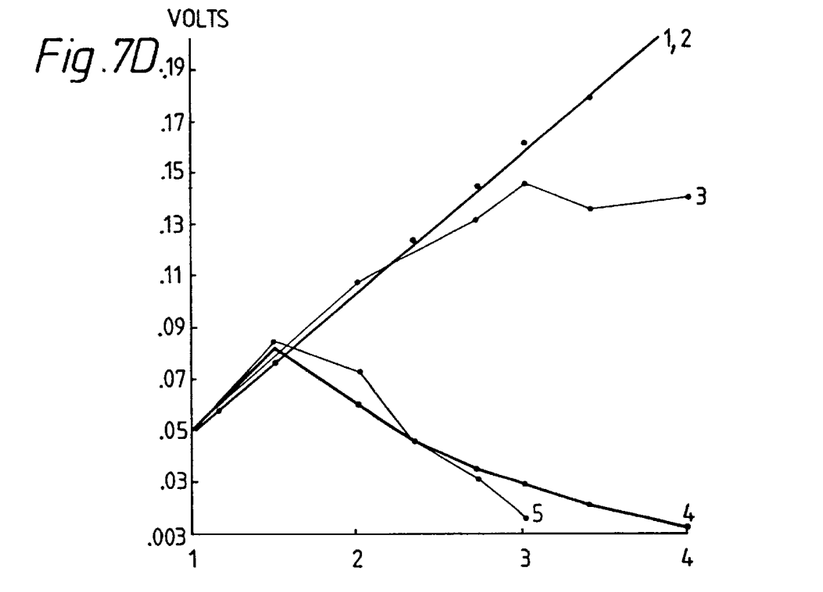

FIG. 7D shows the sensitivity (millivolts versus p[Cl⁻] negative log activity) for electrodes anodised for short times (30 seconds at current densities (for plots 1 to 5) of 0.85, 0.42, 0.21, 0.095, and 0.040 mA/cm² respectively.

It has been found that if the extent of anodisation is fixed in terms of charge per unit area (252 millicoulombs/cm²) then the electrode slope is within the range 57.1–57.2 mV/p[Cl⁻] for a wide range of reciprocally varying anadisation times and current densities (1200–150 seconds, 0.21–1.68 mA/cm²).

Figure 7E:
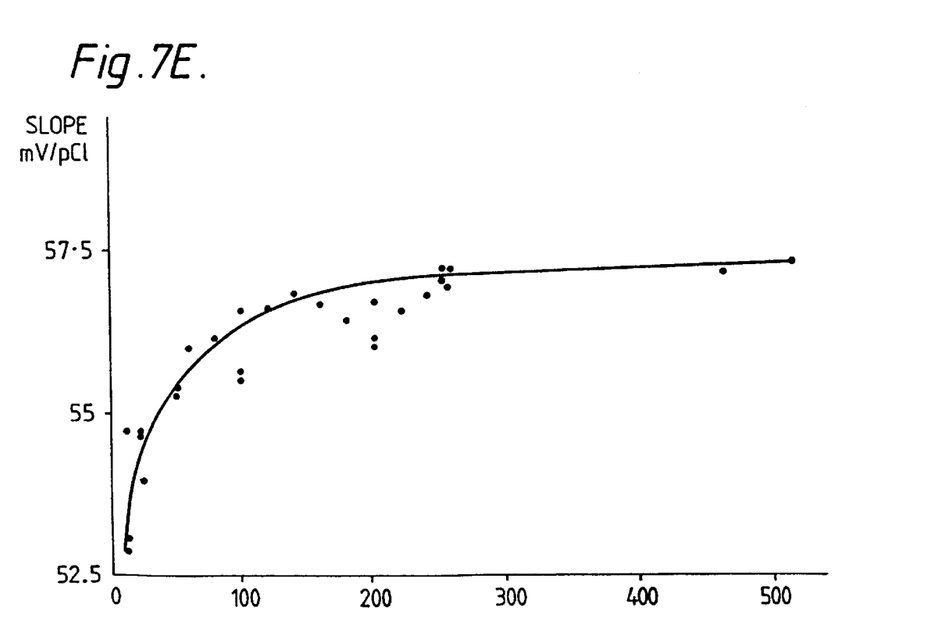

FIG. 7E summarises the electrode sensitivities obtained for a range of anodisation charge densities (slope (mV/p[Cl⁻]) versus charge density (millicoulomb/cm²)).

These graphs indicate among other things the extent to which AgCl needs to be formed to give maximal sensitivity in the resulting electrodes.

It has been found that, provided the formation of AgCl is carried out to an adequate extent for maximal sensitivity, the consistency in the slope (sensitivity) amongst screen-printed anodised Ag/AgCl electrodes is comparable with that of good conventional wire electrodes (54.7–8 mV/p[Cl⁻¹ in comparison with 55.0–1 mV/p[Cl⁻]).

The several features described herein, including those illustrated in and by the drawings, can be used in any desired combinations and variations.

In a further embodiment similar to the method of Example 3, the substrate, a (175×175 mm) PVC sheet, 1.5 mm thick, is cleaned by washing in detergent in an ultrasonic bath followed by copious washing with ultra pure water.

An array of electrodes is then printed onto the substrate using a Dek 245 screen printer together with Johnson Matthey P2300 silver ink. Following printing, the substrate sheets are dryed overnight at 55° C. in an oven.

Figure 1:
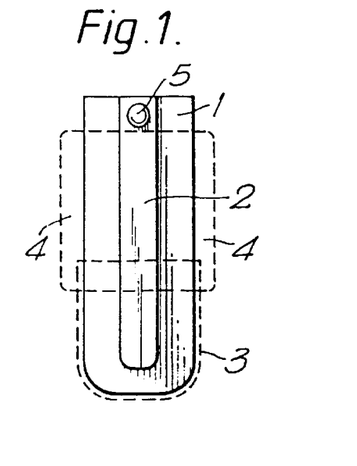
FIG. 1 is a diagrammatic plan view of an electrode structure according to the invention.
Figure 2:
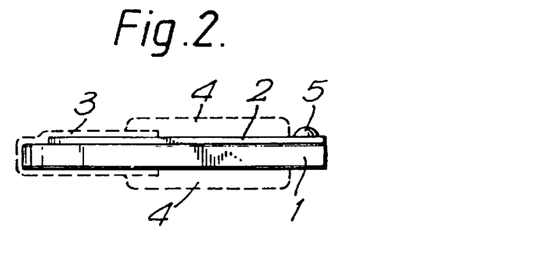
FIG. 2 is a diagrammatic section of the electrode structure of FIG. 1.

Each printed electrode comprises a stripe of silver 3 mm c 25 mm, having an end contact pad for a standard 0.1' pitch edge connector (FIG. 1.).

To make the screen for use on the printer, the pattern art-work is reproduced by photolithography onto a 71/180 (counts per cm/in) polyester mesh screen covered with a 13 um photographic emulsion.

Chloridisation of the electrodes may then be achieved by chemical or electrical methods.

Electrical Chlorodisation

This is an anodisation procedure. A constant current is passed for a known time through a cell comprising a platinum cathode and a planar silver electrode as the anode both dipping into dilute hydrochloric acid solution. With this procedure electrochemically repeatable (potentials constant to 0.1 mV) planar electrodes can be made by anodising in 0.1M hydrochloric acid, using a current density of 1 mA/cm² for 240 seconds. This gives a silver chloride thickness of 1um using the screen printed silver electrodes.

Chemical Chloridisation

Silver chloride can be produced by chemical oxidation of silver in the presence of chloride ion. This procedure is particularly useful for the mass chloridisation of screen printed silver electrodes.

In this example, the electrodes are immersed in a solution containing Hydrochloric acid at 0.1 m concentration and hydrogen peroxide at a concentration of 1 m for a time of 200 seconds. This produces a layer of silver chloride thickness of approximately 1um.

Tests on electrochemically produced silver chloride electrodes have shown standard potential values lying within 0.1 mV of the mean and slope factors varying by 0.3 mV.pCl-. These values have been maintained during the testing of approximately 200 electrodes, giving substantial assurance of the repeatability of these devices.

It has been found that electrodes manufactured in accordance with the methods described in the other examples also have readily repeatable characteristics in terms of standard potential and slope factor.

In all these cases, it is believed that this is a result of the fact that there is no sharply defined boundary between the layers of silver and silver chloride particles. Instead, the boundary is blurred so that the ratio of silver particles to silver chloride particles in the region of interface between the two layers gradually increases from the silver chloride particle layer to the silver particle layer.

We claim:

1. A composite electrode comprising:
   a solid non-conducting substrate;
   metallic particles;
   a non-conductive matrix layer in which the metallic particles are incorporated, and
   insoluble metal salt particles which are of the same metal as the metallic particles, which are incorporated in said non-conductive matrix and which are accessible to reactions with electrochemical reagents at the surface of the electrode, such that there are insoluble metal salt particles located between the metallic particles and the surface of the electrode and the surface of the electrode predominantly comprises metal salt particles whereby the ratio of metallic particles to insoluble metal salt particles gradually increases from the outermost towards the innermost portions of the non-conductive matrix layer.

2. A composite electrode according to claim 1 further comprising an electroactive membrane which overlies said matrix incorporating said metal halide-containing particles.

3. A composite electrode according to claim 1 wherein the metal halide particles are derived from a layer of non-conducting matrix incorporating metallic particles the surface of which layer has been treated to convert metal to metal halide.

4. A composite electrode according to claim 1 wherein the non-conductive matrix has been formed by printing a layer of corresponding material in flowable form onto the solid substrate, and hardening the layer or allowing it to harden.

5. A composite electrode according to claim 1 wherein the substrate is made of plastics or ceramic material.

6. A composite electrode according to claim 5, wherein the substrate is made of a material selected form the group consisting of epoxy, polyvinylchloride, or alumina.

7. A composite electrode according to claim 1 wherein the particles in the matrix comprise silver and silver chloride particles.

8. A composite electrode according to claim 1 wherein a hermetic sealing layer is present over all conductive or electroactive parts of the electrode other than a sensitive surface intended to contact electrolyte.

9. An assembly comprising a composite electrode according to claim 1 wherein the metallic particles of the composite electrode are functionally connected to a hermetically sealed semiconductor device or integrated semiconductor circuit mounted on said solid non-metallic substrate.

10. An assembly according to claim 9 wherein the substrate is made of a ceramic or a polymer and the assembly is encapsulated with a hermetic sealing material which forms an integral sealed assembly having a functionally exposed area or areas not covered by the encapsulation.

11. An assembly according to claim 9, wherein said hermetically sealed semiconductor device or integrated circuit is packaged in a non-metallic package which constitutes said substrate for said composite electrode.

12. An electrode according to claim 1 in which the matrix layer has been produced by printing a layer of metallic particle containing material on the said substrate and hardening the layer or allowing it to harden.

13. A composite electrode comprising:

a solid non-conducting substrate;

metallic particles; and a non-conductive matrix incorporating insoluble salt particles, the salt being of the same metal as the metallic particles and the metal salt particles being accessible to reaction with external electrochemical reagents at the surface of the electrode, wherein the metallic particles are incorporated in said non-conductive matrix, said matrix having been applied directly to said substrate as a metallic particle containing layer and the metal salt particles thereafter being formed therein by treatment of the surface of said matrix layer, such that there are insoluble metal salt particles located between the metallic particles and the surface of the electrode and the surface of the electrode predominantly comprises metal salt particles whereby the ratio of metallic particles to insoluble salt particles gradually increases from the outermost towards the innermost portions of the non-conductive matrix layer.

* * * * *